United States Patent [19]
Kohno et al.

[11] Patent Number: 5,919,340
[45] Date of Patent: Jul. 6, 1999

[54] PROCESS FOR RECOVERING PENTAFLUOROETHANE

[75] Inventors: Satoru Kohno; Takashi Shibanuma, both of Osaka, Japan

[73] Assignee: Daikin Industries Ltd., Osaka, Japan

[21] Appl. No.: 08/776,942

[22] PCT Filed: May 8, 1995

[86] PCT No.: PCT/JP95/00874

§ 371 Date: Feb. 14, 1997

§ 102(e) Date: Feb. 14, 1997

[87] PCT Pub. No.: WO96/05158

PCT Pub. Date: Feb. 22, 1996

[30] Foreign Application Priority Data

Aug. 17, 1994 [JP] Japan .................................. 6-193066

[51] Int. Cl.$^6$ .................................................. B01D 3/34
[52] U.S. Cl. .............................. 203/57; 203/98; 570/178
[58] Field of Search ................................ 570/178, 180; 203/63, 66, 67, 68, 57, 62, 70

[56] References Cited

U.S. PATENT DOCUMENTS

| | | | |
|---|---|---|---|
| 3,101,304 | 8/1963 | Wiist | 203/67 |
| 3,282,801 | 11/1966 | Wiist | 62/632 |
| 3,689,374 | 9/1972 | Hanson | 203/64 |
| 5,087,329 | 2/1992 | Felix | 203/67 |
| 5,200,431 | 4/1993 | Dattani et al. | 570/178 |
| 5,470,442 | 11/1995 | Mahler et al. | 203/56 |

FOREIGN PATENT DOCUMENTS

| | | |
|---|---|---|
| 2124282 | 11/1994 | Canada . |
| 0 669302A1 | 8/1995 | France . |
| WO 9521147 | 8/1995 | WIPO . |
| WO 9521148 | 8/1995 | WIPO . |

*Primary Examiner*—Bernard Dentz
*Assistant Examiner*—Garth M. Dahlen
*Attorney, Agent, or Firm*—Birch, Stewart, Kolasch, & Birch, LLP

[57] ABSTRACT

There is provided a process of effectively separating pentafluorethane (HFC-125) out of a mixture of HFC and chloropentafluoroethane (CFC-115). When the mixture of HFC-125 and CFC-115 is subjected to extractive distillation so as to obtain concentrated HFC-125, methanol, ethanol, butanol, propyl alcohol, pentafluoropropanol, tetrafluoropropanol or acetone is used as an extractant, whereby CFC-115 is obtained as a distillate product and a mixture of HFC-125 and the extractant is separated from HFC-125 by distilling the mixture and re-used in the extractive distillation.

5 Claims, 2 Drawing Sheets

PROCESS FOR RECOVERING PENTAFLUOROETHANE

This applicaton is a 371 of PCT/JP95/00874 filed May 8, 1995.

TECHNICAL FIELD

The present invention relates to a process of producing pentafluoroethane by separating pentafluoroethane out of a mixture comprising at least pentafluoroethane (which is sometimes referred to as HFC-125) and chloropentafluoroethane (which is sometimes referred to as CFC-115) using extractive distillation in which a specific compound is used as an extractant (or solvent). Such a mixture may be for example a reaction product from a production process of pentafluoroethane by fluorinating tetrachloroethylene.

BACKGROUND ART

HFC-125 is a useful compound which can be a substitute for flon which does not contain chlorine, and it is used as a refrigeration medium, a forming agent, a propellant and so on. Fluorination of tetrachloroethylene is employed as a process of producing HFC-125. In such a process, dichlorotetrafluoroethane, dichlorotrifluoroethane, hexafluoroethane, CFC-115 and so on are produced as by-products.

Among those, CFC-115 has a boiling point of −38.7° C. which is considerably close to a boiling point of HFC-125 (−48.5° C.) as an objective product. Further, a relative volatility between these two compounds is near one. Particularly when a mixture contains HFC-125 at a concentration of not less than 95 mol % (thus, CFC-115 is not more than 5 mol %), the relative volatility is about 1.04. Therefore, it requires a distillation apparatus having many plates to separate HFC-125 in its higher concentration out of such a mixture using a conventional distillation operation, which generally means that the separation using the distillation is extremely difficult.

In the present specification, the relative volatility ($\alpha$) is defined as follows when a solution consisting essentially of at least two components A and B in question (a boiling point of component A<a boiling point of component B) is in a vapor-liquid equilibrium state:

$$\alpha=(y_A/x_A)/(y_B/x_B)$$

wherein $x_A$ is a molar fraction of lower boiling component A in the liquid phase, $x_B$ is a molar fraction of higher boiling component B in the liquid phase, $y_A$ is a molar fraction of lower boiling component A in the vapor phase which is equilibrated with the liquid phase and $y_B$ is a molar fraction of the higher boiling component B in such a phase.

Extractive distillation has been employed as a process of separating one component from a mixture of a system of which relative volatility is close to one. With regard to separation of a mixture of HFC-125 and CFC-115, for example U.S. Pat. No. 5,087,329 discloses an extractive distillation process which uses a fluorocarbon containing 1 to 4 carbon atoms as an extractant.

In the process disclosed in U.S. Pat. No. 5,087,329, a relative volatility between HFC-125 and CFC-115 is about 1.2 based on calculation using figures shown in Example 1 thereof. Thus, in order that a concentration of HFC-125 is increased from HFC-125/CFC-115=7/93 (mol %/mol %) to HFC-125/CFC-115=99.7/0.3 (mol %/mol %) using distillation, about 40 theoretical plates are required. The number of the theoretical plates were calculated as explained below.

DISCLOSURE OF INVENTION

The present inventors have studied as to a process in which HFC-125 is further effectively separated out of a mixture comprising HFC-125 and CFC-115 using extractive distillation, and found that when a mixture comprising at least HFC-125 and CFC-115 is subjected to extractive distillation, HFC-125 is effectively (for example, using a distillation column having a very small number of theoretical plates) separated from the mixture by using, as an extractant (or a solvent), at least one compound (thus, as a single compound or a mixture of the compounds) selected from an alcohol containing 1 to 4 carbon atoms, a ketone containing 3 to 7 carbon atoms, an ether containing 2 to 6 carbon atoms and nitromethane or at least one selected from a hydrocarbon containing 3 to 8 carbon atoms, trichloroethylene and carbon tetrachloride.

Thus, the present invention provides a process of separating HFC-125 out of a mixture comprising at least HFC-125 and CFC-115 by subjecting the mixture to extractive distillation so as to obtain HFC-125 in which a CFC-115 concentration is relatively reduced, and preferably highly concentrated HFC-125 which does not substantially contain CFC-115 characterized in that at least one compound selected from an alcohol containing 1 to 4 carbon atoms, a ketone containing 3 to 7 carbon atoms, an ether containing 2 to 6 carbon atoms and nitromethane, or at least one compound selected from a hydrocarbon containing 3 to 8 carbon atoms, trichloroethylene and carbon tetrachloride is used as an extractant.

That is, the present invention provides a process of producing pentafluoroethane in which pentafluoroethane is separated out of a mixture comprising at least pentafluoroethane and chloropentafluoroethane which together constitute a main component of the mixture by subjecting the mixture to extractive distillation so as to obtain a mixture which contains pentafluoroethane as a main component and which does not substantially contain chloropentafluoroethane, which process is characterized in that at least one compound selected from an alcohol containing 1 to 4 carbon atoms, a ketone containing 3 to 7 carbon atoms, an ether containing 2 to 6 carbon atoms and nitromethane, or at least one compound selected from a hydrocarbon containing 3 to 8 carbon atoms, trichloroethylene and carbon tetrachloride is used as an extractant of the extractive distillation, and a mixture comprising pentafluoroethane and the extractant which together constitute a main component of the mixture is obtained as a bottom product provided that at least one compound selected from the alcohol containing 1 to 4 carbon atoms, the ketone containing 3 to 7 carbon atoms, the ether containing 2 to 6 carbon atoms and nitromethane is used as the extractant, or a mixture comprising pentafluoroethane as main component is obtained as a distillate product provided that at least one compound selected from the hydrocarbon containing 3 to 8 carbon atoms, trichloroethylene and carbon tetrachloride is used as the extractant.

Figure 1:
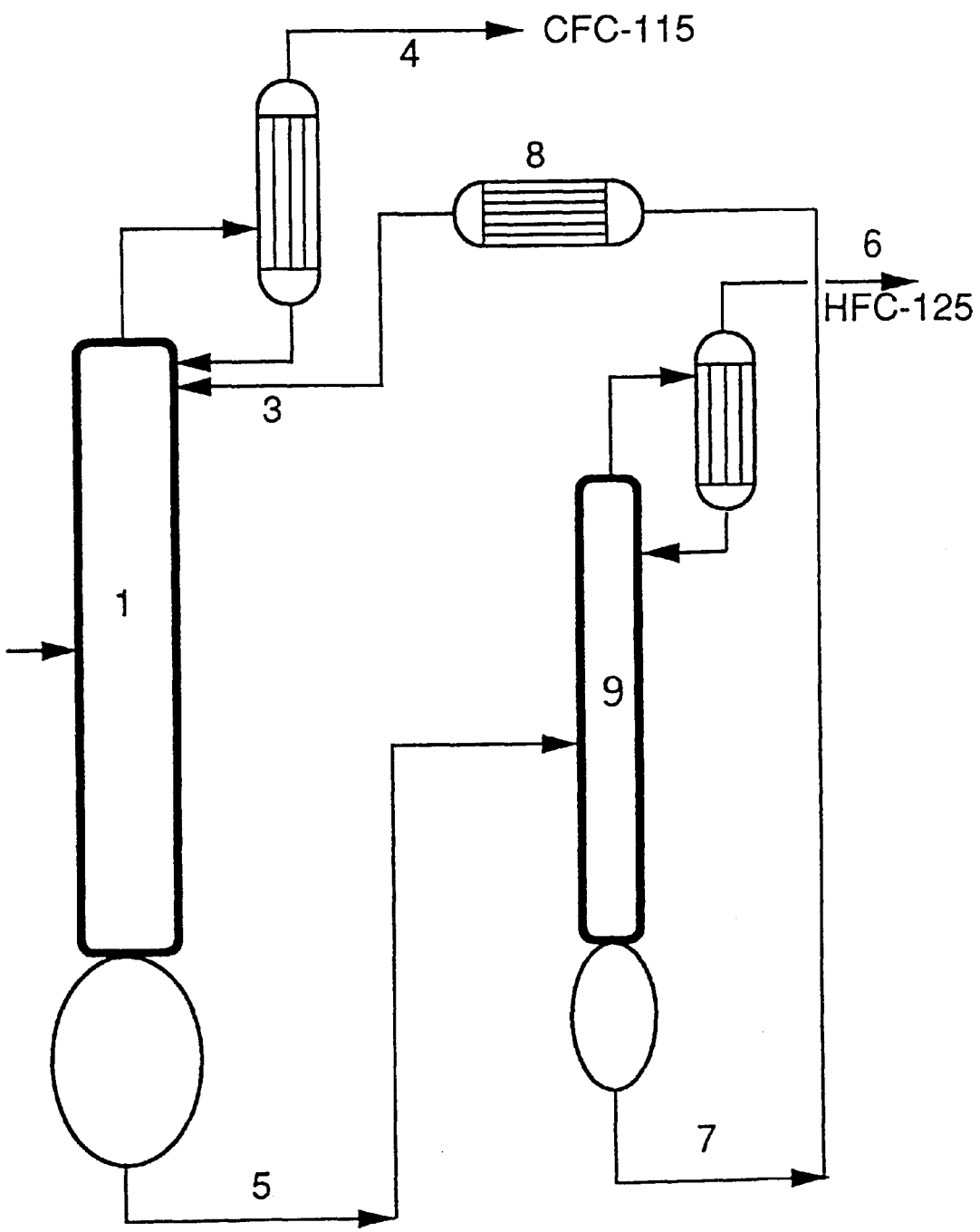
FIG. 1 shows a flow sheet of one embodiment of a separation process in which the process according to the present invention is carried out.

In the drawings, reference numbers denote the following elements, respectively:

1. extractive distillation apparatus
2. mixture which contains HFC-125 and CFC-115
3. extractant
4. distillate product
5. bottom product
6. distillate product
7. bottom product
8. heat exchanger
9. distillation apparatus for HFC-125 separation
11. extractive distillation apparatus
12. mixture which contains HFC-125 and CFC-115
13. extractant
14. distillate product
15. bottom product
16. distillate product
17. bottom product
18. heat exchanger
19. distillation apparatus for extractant recovery

DETAILED DESCRIPTION OF INVENTION

In the present specification, the term "main component" is intended to mean that an amount of the other component rather than the main component is relatively small. It is sufficient that an amount of the main component is concretely not less than 50%, more concretely not less than 60%, and for example not less than 80%. Further, in the present specification, the term "substantially" is intended to mean that a mixture is ultimately obtained in which pentafluoroethane is a main component, for example a mixture in which a concentration of pentafluoroethane is not less than 90% by weight, preferably not less than 99.9% by weight and more preferably not less than 99.99% by weight.

In the present process, when at least one compound selected from the alcohol containing 1 to 4 carbon atoms, the ketone containing 3 to 7 carbon atoms, the ether containing 2 to 6 carbon atoms and nitromethane is used as the extractant, a mixture is obtained as a bottom product which contains pentafluoroethane and the extractant together constituting a main component of the mixture as described above, preferably a mixture in which a concentration of chloropentafluoroethane is not more than 0.1% by weight, and more preferably a mixture in which a concentration of chloropentafluoroethane is not more than 0.01% by weight. In this case, there is no limitation on a composition of a distillate product provided that a ratio of chloropentafluoroethane to pentafluoroethane in the bottom product is reduced from an original ratio thereof, preferably reduced to not more than 1/10 of the original ratio, and more preferably reduced to not more than 1/100 of the original ratio. The distillate product may contain chloropentafluoroethane as a main component thereof, may contain pentafluoroethane as a main component thereof or may contain chloropentafluoroethane and pentafluoroethane which together constitute a main component thereof with the proviso described just above.

In the present process, when at least one compound selected from the hydrocarbon containing 3 to 8 carbon atoms, trichloroethylene and carbon tetrachloride is used as the extractant, a mixture is obtained as a distillate product which contains pentafluoroethane as a main component thereof as described above, preferably a mixture in which a concentration of pentafluoroethane is not less than 99.9% by weight. In this case, there is no limitation on a composition of a bottom product provided that a ratio of pentafluoroethane to chloropentafluoroethane in the distillate product is increased from an original ratio thereof, preferably increased to not less than 10 times of the original ratio, and more preferably increased to not less than 100 times of the original ratio. The bottom product may contain chloropentafluoroethane and the extractant which together constitute a main component of the bottom product, or may contain chloropentafluoroethane pentafluoroethane and the extractant which together constitute a main component of the bottom product with the proviso described just above.

In one embodiment of the present invention, the mixture is of a binary system which consists substantially of HFC-125 and CFC-115.

In another embodiment of the present invention, the bottom product thus obtained, for example one which contains the extractant and pentafluoroethane which together constitute a main component of the bottom product or one which contains chloropentafluoroethane and the extractant which together constitute a main component of the bottom product is subjected to distillation so as to separate into the extractant and pentafluoroethane or chloropentafluoroethane, whereby the extractant is recovered, which may be supplied to and re-used in the extractive distillation step.

In the present specification, the extractive distillation is used in the meaning which is generally used in the field, in particular the field of chemical engineering; for example, it means a distillation operation which is characterized in that addition of a third component to a mixture of a binary system facilitates separation of the mixture due to a relative volatility being considerably deviated from one by means of the third component, otherwise the separation would be difficult when using the conventional distillation.

In the present invention, the alcohol containing 1 to 4 carbon atoms is intended to mean a compound having 1 to 4 carbon atoms which form a main chain and which contains at least one hydroxyl group, such as an aliphatic alcohol having 1 to 4 carbon atoms. Concretely, methanol, ethanol, butanol, propanol, pentafluoropropanol ($C_2F_5CH_2OH$), tetrafluoropropanol ($HCF_2CF_2CH_2OH$), ethylene glycol, propanediol and trifluoroethanol can be exemplified.

In the present invention, the ketone containing 3 to 7 carbon atoms is intended to mean a ketone which is represented by a general formula: $R_1$—CO—$R_2$ (wherein $R_1$ and $R_2$ are aliphatic hydrocarbon groups which may be the same or different from each other, respectively). Concretely, acetone, diethyl ketone and methyl ethyl ketone can be exemplified.

In the present invention, the ether containing 2 to 6 carbon atoms is intended to mean an ether which is of a general formula: $R_1$—O—$R_2$ (wherein $R_1$ and $R_2$ are aliphatic hydrocarbon groups which may be the same or different from each other, respectively). Concretely, diethyl ether, dimethyl ether, methyl ethyl ether and dipropyl ether can be exemplified.

In the present invention, the hydrocarbon containing 3 to 8 carbon atoms includes both of a cyclic hydrocarbon and a chain hydrocarbon. The cyclic hydrocarbon is intended to mean one which contains at least one cyclic structure. Concretely, cyclohexane, cyclopentane, cyclopropane and cyclobutane can be exemplified as a saturated cyclic hydrocarbon. As an unsaturated cyclic hydrocarbon, an aromatic hydrocarbon such as benzene can be exemplified. The chain hydrocarbon also includes both of a saturated one and an unsaturated one, and concretely normal octane and normal hexene can be exemplified. As a mixture thereof, using petroleum ether or petroleum benzine may be particularly preferable.

The present inventors have studied the extractants as described above which are used in the process of separating HFC-125 from the mixture comprising HFC-125 and CFC-115 by extractive distillation, and obtained measurements of the relative volatilities between HFC-125 and CFC-115 which are shown in Table 1 below:

TABLE 1

| | Extractant | Extractant Ratio*) | Relative Volatility ($\alpha$) |
|---|---|---|---|
| (1) | Dichlorotrifluoroethane**) | 0.85 | 1.2 |
| (2) | Dichloropentafluoropropane | 0.67 | 1.2 |
| (3) | Tetrachloroethylene | 1.33 | 1.2 |
| (4) | Dichloromethane | 2.12 | 0.9 |
| (5) | Methanol | 1.60 | 0.4 |
| (6) | Ethanol | 1.5 | 0.5 |
| (7) | Propanol | 1.2 | 0.76 |
| (8) | Butanol | 1.4 | 0.86 |
| (9) | Pentafluoropropanol | 1.2 | 0.88 |
| (10) | Tetrafluoropropanol | 1.6 | 0.65 |
| (11) | Acetone | 0.5 | 0.4 |
| (12) | Cyclohexane | 1.6 | 1.7 |
| (13) | Cyclopentane | 1.5 | 1.9 |
| (14) | Trichloroethylene | 2.0 | 1.4 |
| (15) | Carbon Tetrachloride | 1.6 | 1.5 |
| (16) | Normal Octane | 1.4 | 1.8 |
| (17) | Petroleum Benzine | 4.7 | 2.1 |
| (18) | Petroleum Ether | 4.0 | 2.1 |
| (19) | Diethyl Ether | 1.4 | 0.7 |
| (20) | Nitromethane | 1.4 | 0.4 |

*) Extractant Ratio = weight of extractant/weight of (HFC-125 + CFC-115)
**) Extractant described in U.S. Pat. No. 5,087,329

When the measurements of Table 1 were obtained, the following manner was employed: After a sealed vessel was evacuated to an almost vacuum pressure, predetermined amounts of HFC-125, CFC-115 and the extractant were charged into the vessel, which was allowed to reach a vapor-liquid equilibrium state at a temperature of 20° C. Then, the liquid phase and the vapor phase were analyzed using gas chromatography to obtain compositions of the both phases as molar fractions. The relative volatility $\alpha$ was calculated using the above equation $\alpha=(y_A/x_A)/(y_B/x_B)$.

As clearly seen from Table 1, when the alcohol having 1 to 4 carbon atoms, the ketone having 3 to 7 carbon atoms, the ether having 2 to 6 carbon atoms or nitromethane which is represented by compound (5) to (11), (19) or (20) in Table 1 is used as the extractant, the relative volatility is considerably smaller than one.

In addition, when the hydrocarbon having 3 to 8 carbon atoms, trichloroethylene or carbon tetrachloride which is represented by compounds (12) to (18) in Table 1 is used as the extractant, the relative volatilities are considerably larger than one. Therefore, when HFC-125 is to be separated out of the mixture of HFC-125 and CFC-115 by the extractive distillation using a compound (5) to (20) in Table 1 as the extractant, it is expected that the separation would be carried out using a distillation apparatus which includes much smaller number of theoretical plates than a conventional apparatus.

Generally, when a mixture comprising HFC-125 and CFC-115 is subjected to a distillation operation, HFC-125 is concentrated into an enriching section (a top side of a column) since its boiling point is lower than that of CFC-115. However, when the relative volatility is smaller than 1, for example when one or more compounds from (5) to (11) and (19) and (20) are used as the extractant, CFC-115 is concentrated into the top side of the column.

On the other hand, when one or more compounds from (12) to (18) are used as the extractant, HFC-125 is concentrated into the top side of the column as the distillation apparatus as usual since the relative volatility is larger than 1.

Using the same manner as in the case when the data of Table 1 were obtained, the present inventors further studied effects of a composition of the mixture of HFC-125 and CFC-115 and an extractant ratio on the relative volatility for the case in which the mixture of HFC-125 and CFC-115 is subjected to the extractive distillation using methanol as the extractant, and obtained results shown in Table 2 below:

TABLE 2

(in case using methanol as extractant)

| Weight Ratio of HFC-125/CFC-115 | Extractant Ratio*) | Relative Volatility |
|---|---|---|
| 99.98/0.017 | 1.5 | 0.47 |
| 99.84/0.164 | 2.1 | 0.48 |
| 97.8/2.2 | 3.0 | 0.26 |
| 97.8/2.2 | 1.6 | 0.39 |
| 97.8/2.2 | 0.8 | 0.57 |
| 97.8/2.2 | 0.2 | 0.77 |
| 80.9/19.1 | 1.2 | 0.48 |
| 38.3/61.7 | 1.2 | 0.48 |

*) Extractant Ratio = weight of methanol/weight of (HFC-125 + CFC-115)

It has been confirmed from the results of Table 2 that the alpha ($\alpha$) is considerably smaller than one in all the weight ratios, so that the addition of methanol into the mixture of HFC-125 and CFC-115 at various extractant ratios leads to effective separation of CFC-115 as a volatile component, namely methanol is preferable as the extractant when separation of the HFC-125/CFC-115 mixture is carried out using the extractive distillation.

Then, the separation process of the present invention will be hereinafter compared with Example described in U.S. Pat. No. 5,087,329 as to the number of theoretical plates of an extractive distillation column which is required for example when concentrated HFC-125 (e.g. a mixture of HFC-125 (99.9 mol %)/CFC-115 (0.1 mol %)) is to be obtained from a mixture of HFC-125 (90 mol %)/CFC-115 (10 mol %).

The process described in the above U.S. Patent requires about 26 theoretical plates in order to produce a top distillate product of concentrated HFC-125 (e.g. concentrated to a mixture of HFC-125 (99.9 mol %)/CFC-115 (0.1 mol %)). In this case, calculation was carried out assuming the relative volatility to be 1.2. To the contrary, when according to the present process the extractant such as those (12) to (18) is used which makes the relative volatility larger than one, the required number of theoretical plates is about eight. In this case, calculation was carried out assuming the relative volatility to be 1.9.

When according to the present process the extractant such as those (5) to (11) and (19) and (20) is used which makes the relative volatility smaller than one, CFC-115 is concentrated into the top side of the column as a low boiling component. When the column has about six theoretical plates, a mixture of the extractant and HFC-125 which is concentrated to a ratio of HFC-125 (99.9 mol %)/CFC-115 (0.1 mol %) as a distillate product is produced as a bottom product while a mixture is produced in which a concentration of CFC-115 is increased from its original concentration to a ratio of HFC-125 (80 mol %)/CFC-115 (20 mol %). In this case, calculation was carried out assuming the relative volatility to be 0.4.

The required number (N) of the theoretical plates referred to in the above was calculated according to the following equation:

$$\alpha^N = (y_W/x_W)/(y_D/x_D)$$

wherein $\alpha$ is a relative volatility, $x_D$ is a molar fraction of HFC-125 in a top distillate product, $x_W$ is a molar fraction of HFC-125 in a bottom (or still) product, $y_D$ is a molar fraction of CFC-115 in a top distillate product and $y_W$ is a molar fraction of CFC-115 in a bottom (or still) product.

When the extractant is used which makes the relative volatility smaller than one, HFC-125 should be separated from the extractant so as to finally obtain HFC-125 alone since the bottom product from the extractive distillation step contains the extractant as described above. This separation is easily carried out with a conventional distillation operation using a plate column or a packed column since a boiling point difference is large between HFC-125 and the extractant. Thus, HFC-125 is effectively separated out of the mixture comprising at least HFC-125 and CFC-115 by using combination of the extractive distillation operation with the distillation operation thereafter which separates the extractant.

Also, when the extractant is used which makes the relative volatility larger than one, the bottom product of the extractive distillation step contains the extractant as described above. In this case, objective HFC-125 is produced as the distillate product of the extractive distillation step, and thus, any treatment of the bottom product is possible. Preferably, the extractant is recovered from the bottom product using for example distillation and re-used in the extractive distillation step.

If the mixture to be separated contains a third component in addition to HFC-125 and CFC-115, only difference is resides in that the third component behaves together with HFC-125 and/or CFC-115 depending on a boiling point of the third component. Thus, even if the third component is contained in the mixture, HFC-125 is separated from CFC-115 by carrying out the extractive distillation using the extractant according to the present invention.

Further, with respect to the re-use of the extractant in the extractive distillation step, when the extractant disclosed in U.S. Pat. No. 5,087,329 is used, CFC-115 is concentrated into the bottom product and the extractant is also recovered from the distillation bottom. This means that the extractant contains a large amount of CFC-115, which necessitates complete separation of CFC-115 for the re-use of the extractant. If only a small amount of CFC-115 remains in the extractant, CFC-115 may be ultimately added to the extractive distillation step, whereby extraction efficiency may deteriorate and the required number of the theoretical plate may increase. In fact, it is estimated that the required number of the theoretical plate of a distillation apparatus would be about 10 to 20 in order to separate CFC-115 while the extraction efficiency does not deteriorate. With this regard, this is also applicable when the cyclic hydrocarbon is used as the extractant in the process of the present invention.

On the other hand, in the process according to the present invention in which the extract such as the compound (5) to (11) and (19) or (20) is used which makes the relative volatility smaller than one, for example, the bottom product from the extractive distillation step does not substantially contain CFC-115 so that it is sufficient to separate only HFC-125 from the extractant. Therefore, even though HFC-125 remains in the extractant at a concentration of few percentages and such extractant is re-used in the extractive distillation step, almost no effect is observed on the extraction efficiency. Thus, the number of theoretical plate of the distillation apparatus required for the recovery of the extractant is only about 2 to 5. From this view point, it is preferable in the process of the present invention to used at least one selected from the alcohol containing 1 to 4 carbon atoms, the ketone containing 3 to 7 carbon atoms, the ether containing 2 to 6 carbon atoms and nitromethane is used as the extractant.

The extractive distillation process using the compound as the extractant according to the present invention can be carried out any distillation apparatus which is conventionally used such as a plate column, a packed column and so on. There are no specific limitations on various conditions of the distillation apparatus (such as an operation temperature, an operation pressure, a reflux ratio, a total plate number of the distillation apparatus, plate levels of mixture feed and extractant feed and so on), and proper conditions are selected depending on aimed separation. Since HFC-125 and CFC-115 have considerably low boiling points, it is generally preferable to carry out the extractive distillation under a pressurized condition. The operation pressure may be for example in the range between 0 and 30 Kg/cm$^2$-G (gauge pressure), and preferably in the range between 10 and 20 Kg/cm$^2$-G. Temperatures at the top and the bottom of the distillation apparatus are determined depending on the operation pressure and compositions of the distillate product and the bottom product. In order to carry out the distillation operation economically considering operation temperatures of a condenser and a reboiler, the temperature at the top of the distillation apparatus is preferably in the range between −40° and 50° C., and the temperature at the bottom of the distillation apparatus is preferably in the range between −20° and 70° C.

The process of the present invention may be carried out in a batch mode or a continuous mode. Although in some cases, the process may be carried out in a semi-continuous mode wherein withdrawal and/or feed is carried out intermittently, the extractant should be continuously supplied to the distillation apparatus.

In the process of the present invention, a ratio (S/F) of an amount (S) of the extractant to an amount (F) of the feed mixture (namely, HFC-125 and CFC-115) has an effect on an extent of the separation. Generally, the ratio may be properly selected depending on a composition of HFC-125/CFC-115 of the mixture to be subjected to the extractive distillation, an allowable concentration of CFC-115 which remains in the separated HFC-125 and so on. A required number of theoretical plate of the extractive distillation apparatus may be properly selected in combination with the selection of the ratio (S/F).

Preferable separation may be usually achieved with the ratio based on weight in the range between about 0.1 and 20, and preferably in the range between about 1 and 10. For example, the following example can be shown: A mixture of CFC-115 (1 mol %) and HFC-125 (99 mol %) is subjected to the extractive distillation using the extractant selected from the compounds (5) to (11) and (19) and (20), whereby CFC-115 is distilled in a concentration increased to 10 mol % (thus, 90 mol % of HFC-125) and also an HFC-125 stream is finally obtained of which CFC-115 concentration is not more than 0.1 mol % (thus, more than 99.9 mol % of HFC-125) after the separation from the extractant. In order to achieve this separation, it is sufficient that the required number of theoretical plate in the extractive distillation is in the range of for example about 5 to 30 and the weight ratio of the extractant to the mixture consisting of HFC-125 and CFC-115 is in the range of for example about 1 to 10.

BEST MODE FOR CARRYING OUT THE INVENTION

The present invention will be explained in detail with reference to FIG. 1 by way of an example in which methanol is used as the extractant which makes the relative volatility between HFC-125 and CFC-115 smaller than 1.

A mixture 2 comprising HFC-125 and CFC-115 (for example HFC-125/CFC-115=90 mol %/10 mol %) is supplied to an extractive distillation apparatus 1 which is operated under a pressurized condition (for example 15 Kg/cm$^2$-G). For example, an apparatus having the number of theoretical plate of about ten is used as the distillation apparatus 1. Methanol 3 is supplied to the distillation apparatus 1 (for example, onto the first theoretical plate from the top). An amount of methanol is for example about five times by weight of that of the mixture 2. When, under those conditions, the mixture is supplied for example onto the fifth theoretical plate from the top and a reflux ratio is set for ten, whereby a mixture of HFC-125/CFC-115 (for example 10 mol %/90 mol %) is withdrawn from the top as a distillate product 4.

In addition, a mixture containing methanol and HFC-125/CFC-115 (for example 99.9 mol %/0.1 mol %) is withdrawn from the bottom as a bottom product 5 (methanol concentration is 85%). Then, the bottom product is supplied to a distillation apparatus 9 which is operated under a pressurized condition (for example 12 Kg/cm$^2$-G), and HFC-125 is obtained as a distillate product 6 from the top which contains substantially neither methanol nor CFC-115. Methanol which does not substantially contain HFC-125 is recovered from the bottom of the distillation apparatus 9 as a bottom product 7, which is supplied to the extractive distillation apparatus 1 to reuse as the extractant. Methanol to be re-used may be supplied to the distillation apparatus 1 optionally after it is heated or cooled as required through a heat exchanger 8.

In the process of the present invention, the level of the plate onto which the extractant is supplied is preferably above a plate onto which the mixture is supplied in any of the extractants is used. Thus, the plate onto which a reflux is returned and the plate onto which the extractant is supplied may be the same. Optionally, the plate onto which the mixture is fed and the plate onto which the extractant is supplied may be the same. Alternatively, before the mixture is fed to the distillation apparatus, it may be mixed with the extractant and then the resulted mixture may be supplied to the distillation apparatus.

Concretely, when methanol is used as the extractant, it is more preferable to supply methanol onto a plate which is located about 3 to 5 theoretical plates above a plate onto which the mixture is supplied.

Employing the apparatus and the operation conditions as described above, HFC-125 which does not substantially contain CFC-115 can be separated out of the mixture which contains HFC-125 and CFC-115.

Figure 2:
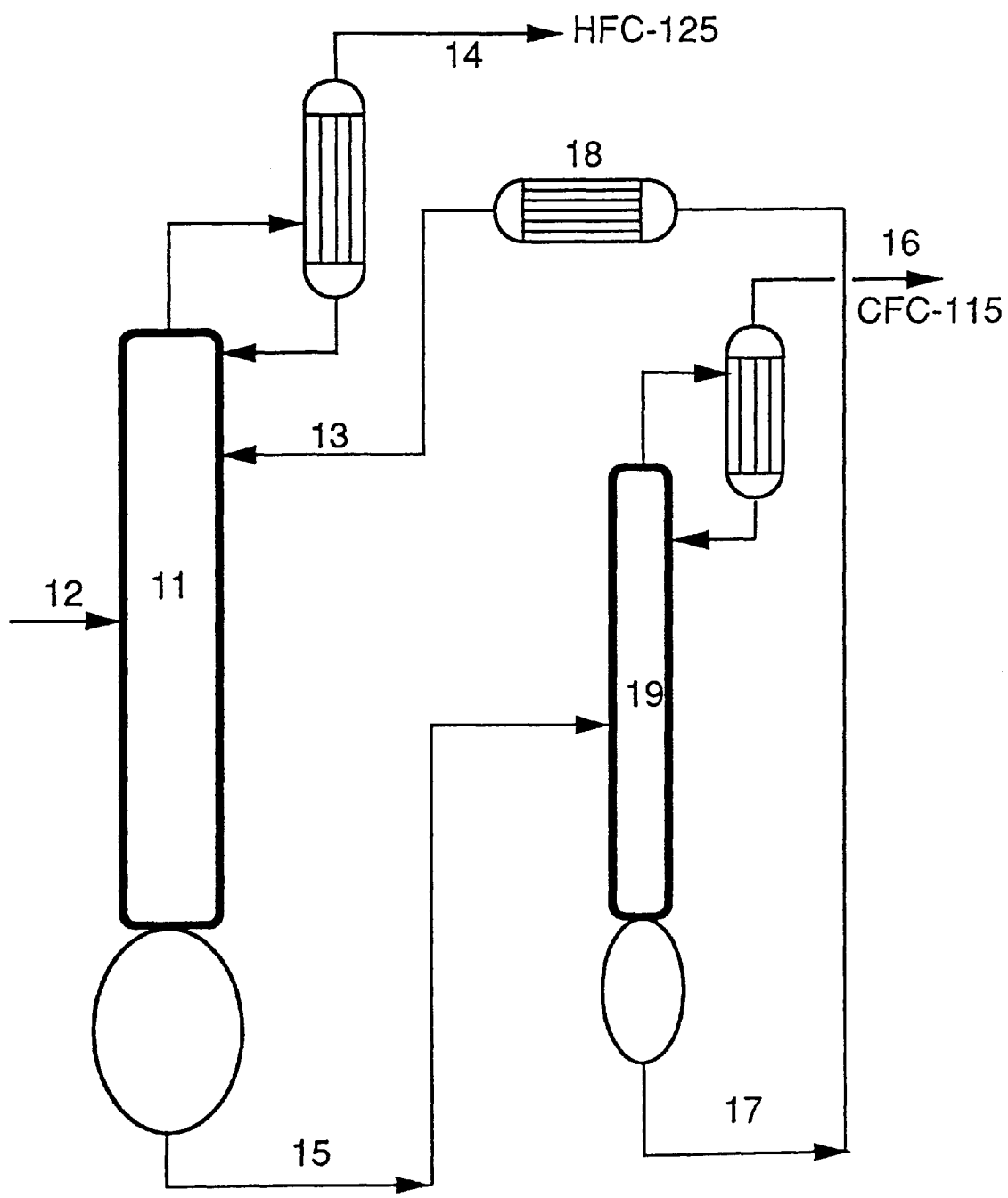
FIG. 2 shows a flow sheet of another embodiment of a separation process in which the process according to the present invention is carried out.

Next, the present invention will be explained in detail with reference to FIG. 2 by way of another example in which cyclopentane is used as the extractant which makes the relative volatility between HFC-125 and CFC-115 larger than 1 as in the cases of the compounds (12) to (18).

A mixture 12 comprising HFC-125 and CFC-115 (for example HFC-125/CFC-115=90 mol %/10 mol %) is supplied to an extractive distillation apparatus 11 which is operated under a pressurized condition (for example 15 Kg/cm$^2$-G). For example, an apparatus having the number of theoretical plate of about twenty is used as the distillation apparatus 11. Cyclopentane 13 is supplied to the distillation apparatus 11 (for example, onto the fifth theoretical plate from the top). An amount of cyclopentane is for example about three times by weight of that of the mixture 12. When, under those conditions, the mixture 12 is supplied for example onto the thirteenth theoretical plate from the top and a reflux ratio is set for ten, whereby a mixture of HFC-125/CFC-115 (for example 99.9 mol %/0.01 mol %) is withdrawn from the top as a distillate product 14.

In addition, a mixture containing cyclopentane and HFC-125/CFC-115 (for example 10 mol %/90 mol %) is withdrawn from the bottom as a bottom product 15 (cyclopentane concentration is 70%). Then, the bottom product is supplied to a distillation apparatus 19 which is operated under a pressurized condition (for example 12 Kg/cm$^2$-G), and a mixture of HFC-125 and CFC-115 (10 mol %/90 mol %) is obtained as a distillate product 16 from the top which does not substantially contain cyclopentane.

Cyclopentane which contains substantially neither HFC-125 nor CFC-115 is recovered from the bottom of the distillation apparatus 19 as a bottom product 17, which is supplied to the extractive distillation apparatus 11 to re-use as the extractant. Cyclopentane to be re-used may be supplied to the distillation apparatus 11 optionally after it is heated or cooled as required through a heat exchanger 18.

The level of the plate onto which cyclopentane is supplied is preferably above a plate onto which the mixture is supplied as described above. It is more preferable to supply cyclopentane onto a plate which is located about 7 to 10 theoretical plates above a plate onto which the mixture is supplied.

Employing the apparatus and the operation conditions as described above, HFC-125 which does not substantially contain CFC-115 can be separated out of the mixture which contains HFC-125 and CFC-115.

EXAMPLE

Using an extractive distillation column equipped with a condenser at its top, a mixture of HFC-125 and CFC-115 (=99/1 (wt/wt)) was treated. The distillation column had a diameter of 100 mm and 10 theoretical plates (actual plate number was 15), and it was operated under a pressure of about 7 Kg/cm$^2$-G (at the column top). Methanol was supplied onto the second plate from the top as the extractant, and the mixture to be distilled was fed at a temperature of 38° C. onto the fifth plate from the top.

Concentrated CFC-115 which contains HFC-125 was withdrawn as a distillate product from the top. This operation was carried out at a reflux ratio of 200. A mixture of HFC-125 and methanol was withdrawn from the bottom at a temperature of 45° C. which does not substantially contain CFC-115.

Mass balance of the above operation is shown Table 3 below:

TABLE 3

|  | total flow rate (Kg/hr) | HFC-125 (wt %) | CFC-115 (wt %) | methanol (wt %) |
|---|---|---|---|---|
| (input) |  |  |  |  |
| Extractant (methanol) | 50 |  |  | 100 |
| HFC-125/CFC-115 mixture | 10 | 99 | 1 |  |
| (output) |  |  |  |  |
| Distillate product | 1 | 89 | 9.9 | 1.1 |
| Bottom product | 59 | 14.9 | 0.01 | 85 |

The bottom product withdrawn from the bottom of the distillation apparatus which contained HFC-125 and methanol and small amount of CFC-115 was supplied to another distillation apparatus having a diameter of 80 mm and 5 theoretical plates (the number of actual plate was 7) which was operated under an operation pressure of 5 $Kg/cm^2$-G and a reflux ratio of 10, whereby HFC-125/CFC-115 (wt/wt) was obtained from the top and methanol as a bottom product. The concentration of CFC-115 in the bottom product contained was not more than 0.01% by weight. This methanol can be re-used as the extractant of the extractive distillation.

We claim:

1. A process of recovering pentafluoroethane by subjecting a mixture comprising at least pentafluoroethane and chloropentafluoroethane to an extractive distillation step so as to obtain pentafluoroethane which does not substantially contain chloropentafluoroethane, which process is characterized by supplying the mixture to the extractive distillation step, supplying, as an extractant to the extractive distillation step, nitromethane, obtaining a mixture comprising pentafluoroethane and the extractant which together constitute a main component of the mixture as a bottom product from the extractive distillation step, or a mixture comprising pentafluoroethane as a main component of the mixture as a distillate product from the extractive distillation step.

2. The process according to claim 1 wherein the mixture and the extractant are mixed together, which is then supplied to the extractive distillation step.

3. The process according to claim 1 or 2 wherein a weight ratio (S/F) of the extractant (S) used in the extractive distillation step to pentafluoroethane and chloropentafluoroethane (F) which are contained in the mixture to be supplied to the extractive distillation step is in the range between 0.1 and 10.

4. The process according to claim 1 wherein pentafluoroethane is separated by distilling the mixture as the bottom product comprising pentafluoroethane and the extractant which together constitute the main component of the mixture, whereby a mixture which contains the extractant as a main component thereof is recovered and re-used in the extractive distillation step.

5. The process according to claim 1 wherein the extractant makes a relative volatility ($\alpha$) between pentafluoroethane and chloropentafluoroethane not larger than one.

* * * * *